(12) United States Patent
Tomaschko et al.

(10) Patent No.: US 7,217,278 B2
(45) Date of Patent: *May 15, 2007

(54) BALLOON CONES AND WAISTS THINNING METHODOLOGY

(75) Inventors: Daniel Keith Tomaschko, Savage, MN (US); Daniel James Horn, Shoreview, MN (US); Xiao Kang Zhang, Champlin, MN (US); Nao Pao Lee, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/781,388

(22) Filed: Feb. 13, 2001

(65) Prior Publication Data

US 2001/0011178 A1    Aug. 2, 2001

Related U.S. Application Data

(60) Division of application No. 09/401,618, filed on Sep. 22, 1999, now Pat. No. 6,193,738, which is a continuation-in-part of application No. 09/076,252, filed on May 11, 1998, now Pat. No. 6,024,752.

(51) Int. Cl.
*A61M 29/00* (2006.01)
*A61F 11/00* (2006.01)

(52) U.S. Cl. .................................................. 606/194

(58) Field of Classification Search ............... 606/192, 606/194, 191, 198, 196, 195, 108; 604/96, 604/101, 102, 103, 53, 259–264; 609/101.4
See application file for complete search history.

(56) References Cited

U.S. PATENT DOCUMENTS

| | | | |
|---|---|---|---|
| 4,413,989 A | 11/1983 | Schjeldahl et al. | |
| 4,456,000 A | 6/1984 | Schjeldahl et al. | |
| 4,490,421 A | 12/1984 | Levy | |
| RE32,983 E | 7/1989 | Levy | |
| 4,906,241 A * | 3/1990 | Noddin et al. | 606/194 |
| 4,906,244 A | 3/1990 | Pinchuk et al. | |
| 4,960,410 A * | 10/1990 | Pinchuk | 604/96.01 |
| 4,963,313 A | 10/1990 | Noddin et al. | |
| RE33,561 E | 3/1991 | Levy | |
| 5,087,394 A | 2/1992 | Keith | |
| 5,108,415 A | 4/1992 | Pinchuk et al. | |
| 5,156,612 A | 10/1992 | Pinchuk et al. | |
| 5,163,989 A | 11/1992 | Campbell et al. | |
| 5,270,086 A | 12/1993 | Hamlin | |
| 5,304,340 A | 4/1994 | Downey | |
| 5,334,146 A | 8/1994 | Ozasa | |
| 5,358,486 A | 10/1994 | Saab | |

(Continued)

OTHER PUBLICATIONS

TG-12X3 Centerless Grinder (Date Unknown).

*Primary Examiner*—Vy Bui
(74) *Attorney, Agent, or Firm*—Vidas, Arrett & Steinkraus, P.A.

(57) ABSTRACT

Medical balloons and balloon preforms are made by methods which include the step of selectively removing material from the proximal and/or distal ends of a segment. In the case of a thermoplastic material characterized by one or more glass transition temperatures, the segment may optionally be maintained at a temperature below the glass transition temperature of the segment during the material removal step.

21 Claims, 4 Drawing Sheets

U.S. PATENT DOCUMENTS

| | | | |
|---|---|---|---|
| 5,415,635 A | 5/1995 | Bagaoisan et al. | |
| 5,443,495 A | 8/1995 | Buscemi et al. | |
| 5,447,497 A | 9/1995 | Sogard et al. | |
| 5,470,313 A | 11/1995 | Crocker et al. | |
| 5,512,051 A | 4/1996 | Wang et al. | |
| 5,514,092 A | 5/1996 | Forman et al. | 604/101 |
| 5,525,388 A * | 6/1996 | Wand et al. | 428/36.9 |
| 5,556,383 A * | 9/1996 | Wang et al. | 604/103.11 |
| 5,587,125 A | 12/1996 | Roychowdhury | 264/515 |
| 5,681,522 A | 10/1997 | Roychowdhury | |
| 5,733,301 A * | 3/1998 | Forman | 606/192 |
| 5,746,644 A | 5/1998 | Cheetham | |
| 5,797,878 A | 8/1998 | Bleam | |
| 5,807,520 A | 9/1998 | Wang et al. | |
| 5,826,588 A * | 10/1998 | Forman | 128/898 |
| 6,024,722 A * | 2/2000 | Rau et al. | 604/96.01 |
| 6,258,099 B1 * | 7/2001 | Mareiro et al. | 604/96.01 |
| 6,287,506 B1 | 9/2001 | Hudgins et al. | 264/515 |
| 6,488,654 B2 | 12/2002 | Gonzalez et al. | 604/103.06 |

* cited by examiner

BALLOON CONES AND WAISTS THINNING METHODOLOGY

CROSS-REFERENCE TO RELATED APPLICATIONS

This application is a Divisional application of U.S. application Ser. No. 09/401,618 filed Sept. 22, 1999 now U.S. Pat. No. 6,193,738 which is a Continuation-in-part application of application Ser. No. 09/076,252 filed May 11, 1998 and issued as U.S. Pat. No. 6,024,752, the contents of both of which are hereby incorporated by reference.

BACKGROUND OF THE INVENTION

The present invention relates to a method for making balloons for catheters used in medical dilatation procedures.

Balloon catheters are being used extensively in procedures related to the treatment of blood vessels. For example, arterial stenosis is commonly treated by angioplasty procedures which involve inserting balloon catheters into specific arteries. Balloon catheters have also been found useful in procedures involving dilation of body cavities.

The most widely used form of angioplasty makes use of a dilatation catheter which has an inflatable balloon at its distal end. Using fluoroscopy, a physician guides the catheter through the vascular system until the balloon is positioned across the stenoses. The balloon is then inflated by supplying liquid under pressure through an inflation lumen to the balloon. The inflation of the balloon causes stretching of a blood vessel and pressing of the lesion into the blood vessel wall to reestablish acceptable blood flow through the blood vessel.

In order to treat very tight stenoses with small openings, there has been a continuing effort to reduce the profile of the catheter so that the catheter can reach and pass through the small opening of the stenoses. There has also been an effort to reduce the profile of the catheter after an initial use and deflation of the balloon to permit passage of the catheter through additional lesions that are to be treated or to allow entry and retreatment of lesions that reclose after initial treatment.

One factor manipulated to reduce the profile of the dilatation catheter is the wall thickness of the balloon material. Balloons for dilatation balloon catheters have been made from a wide variety of polymeric materials. Typically the balloon wall thicknesses have been on the order of 0.0003 to 0.003 inches for most materials. There have been continuing efforts, however, to develop ever thinner walled balloon materials, while still retaining the necessary distensibility and burst pressure rating, so as to permit lower deflated profiles.

The profile of the deflated balloon is limited by the thickness of the waist and cone portions of the balloon. Usually, the waist and cone wall thicknesses are thicker than that of the body of the balloon due to the smaller diameter of the waist and cone portions. In order to reduce the overall profile of the deflated balloon, reduction of the wall thickness of the waist and cone portions must be addressed.

Prior art balloon forming techniques involve stretching and blowing of the balloon from a segment of extruded polymer tubing. Balloons produced by stretching and blowing a tubular preform or "parison" typically have much thicker balloon waist and cone walls than the wall thickness of their body portions. The thicker cone walls contribute to the overall thickness of the catheter, making tracking, crossing and recrossing of lesions more difficult. Further, thick cones interfere with refolding of the balloon on deflation so that the deflated balloon can only be further inserted or withdrawn with difficulty, occasionally even damaging the blood vessel. Thin wall thicknesses enable the deflated balloon to remain narrow, making it easier to advance the balloon through the arterial system.

There have been several solutions proposed for reducing the cone or waist thickness of catheter balloons in U.S. Pat. Nos. 4,906,241, 5,087,394, 5,304,340, EP 318,919 and EP 485,903. U.S. Pat. No. 4,906,241 to Noddin, disclose heating a portion of the balloon preform to a desired temperature and drawing the segment so as to form a necked down region while maintaining a portion of the preform in a crystalline state. The preform may then be blown into a balloon. U.S. Pat. No. 5,304,340 to Downey discloses a method of making a dilatation balloon employing a reverse temperature gradient across the sidewall of a parison and drawing and expanding the parison subject to the temperature gradient.

EP 318,919 to Noddin et al. discloses a procedure in which a portion of the tube is crystallized to render it dimensionally stable under heated conditions. The portion stabilized cannot be appreciably inflated or drawn. The tube is heated in a heated bath and as one end is secured in place the other is drawn to a desired length and in the process is necked-down. The tube is drawn down to a constant diameter sleeve. After the initial necking-down of the tube, the tube is reversed in the bath and the second necked-down portion is formed by the same procedure. After the preform is complete the tube is submerged horizontally and restrained at both ends. Two conical portions at opposing ends are arranged to define the shape of the tapered sections of the balloon. Simultaneously the tube is drawn and expanded without constraint until the molecules of the wall material in the balloon region become stabilized in a biaxially oriented condition. The portions of the tube having the preform tapers expand until they are constrained to the shape of the constraining cones.

U.S. Pat. No. 5,087,394 discloses a method of forming a balloon wherein a length of polymer tubing is formed by drawing the tubing material from an extruder using an extruder die and then irradiated. The method involves positioning an internal support mandrel within the tubing and compressing a portion of the intermediate segment onto the mandrel with a body clamp. The end segment is heated and stretched longitudinally to the desired length. The process of pulling the tube through a restricted hot die or body clamp forms the necked portions and thin waist segments. The other end segment is optionally stretched in a similar manner. The tubing is then heated, and radially stretched by blow-molding to define the balloon and cooled.

EP 485,903 describes a method wherein a tubular parison is formed of a drawable or orientable polymer. It is heated in a metal mold in the range from the second-order transition temperature to the first-order transition temperature of the polymer used. The parison is stretched in the direction of its axis and then inflated radially resulting in a biaxially-drawn or biaxially oriented crude balloon. The parison is then cooled below the second-order transition temperature and deflated. The tapered portions of the crude balloon are redrawn by stretching to reduce their wall thicknesses. The balloon is inflated again and heated above the second transition temperature and then cooled.

The Levy patents (U.S. Pat. No. Re 32,983 and Re Pat. No. 33,561) teach drawing the tubing by axially pulling the tube in a uniform manner apart and then expanding the tube with fluid in a confining apparatus. The stretch process occurs at a temperature above the glass transition temperature and below the melting temperature of the tubing material.

Another method of reducing the cone thickness of balloons is disclosed in U.S. Pat. No. 5,826,588 to Forman, the contents of which are incorporated herein in their entirety by reference. An excimer laser is used to remove portions of the cones from a balloon via photochemical ablation. This materials removal process occurs after the balloon has been formed.

It is possible to make balloons from a variety of materials that are generally of the thermoplastic polymeric type. Such materials may include: polyethylenes, ionomers, ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; copolyesters; thermoplastic rubbers; silicone-polycarbonate copolymers; polyamides; and ethylene-vinyl acetate copolymers. Orientable polyesters, especially polyethylene terephthalate (PET), are among the preferred materials for forming catheter balloons.

Other references illustrating the materials and methods of making catheter balloons include: U.S. Pat. Nos. 4,456,000 to Schjeldahl et al, U.S. Pat. No. 4,490,421, U.S. Re Pat. Nos. 32,983 and 33,561 to Levy, and U.S. Pat. Nos. 4,906,244, 5,108,415, 5,156,621 to Pinchuck et al. and U.S. Pat. No. 5,807,520 to Wang et al.

All US patents and applications and all other published documents mentioned anywhere in this application are incorporated herein by reference in their entirety.

SUMMARY OF THE INVENTION

There remains a need to continue to improve balloon wall strengths while simultaneously reducing their wall thickness. The present invention addresses these needs by reducing the wall thickness of cone and waist portions. The resulting balloon is smaller in size for easier insertion into the body lumen.

The present invention in one aspect is directed to a method comprising the steps of providing a segment of thermoplastic material having a predetermined wall thickness and length, removing material from a portion of at least one of the distal and proximal ends of the segment to achieve a desired reduced thickness while maintaining the temperature of substantially all of the segment below the glass transition temperature of the thermoplastic material or below the highest glass transition temperature if the material is a block copolymer so as to form a balloon preform.

The method may additionally comprise the step of drawing the preform to a predetermined length. Desirably, during the drawing step, the wall thickness of the center portion does not substantially change and the proximal and distal ends form a first cone and waist and a second cone and waist, respectively. Also desirably during the drawing, the temperature of the segment is maintained below the glass transition temperature of the thermoplastic material or below the highest glass transition temperature if the material is a block copolymer so as to form a balloon preform.

The method may additionally comprise the step of expanding the balloon preform in a mold to produce a balloon, the balloon having a body portion, wherein the center portion of the segment becomes the balloon body portion.

In accordance with the inventive method, the removing step may be accomplished via a variety of techniques including grinding and etching.

The invention is also directed to balloon preforms and balloons made in accordance with the inventive methods.

The invention is also directed to a medical balloon having a proximal waist portion, a proximal cone portion, a body portion, a distal cone portion and a distal waist portion wherein at least one of the proximal cone and waist wall thicknesses and distal cone and waist wall thicknesses is less than the body wall thickness, at least one of the proximal waist and cone portions and distal waist and cone portions having had material removed therefrom.

The invention is also directed to a medical balloon having a distal cone with a wall thickness of the distal cone which is less than the wall thickness of the proximal cone.

The invention is also directed to a medical balloon which when inflated has a constant wall thickness over substantially the entire length of the balloon.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
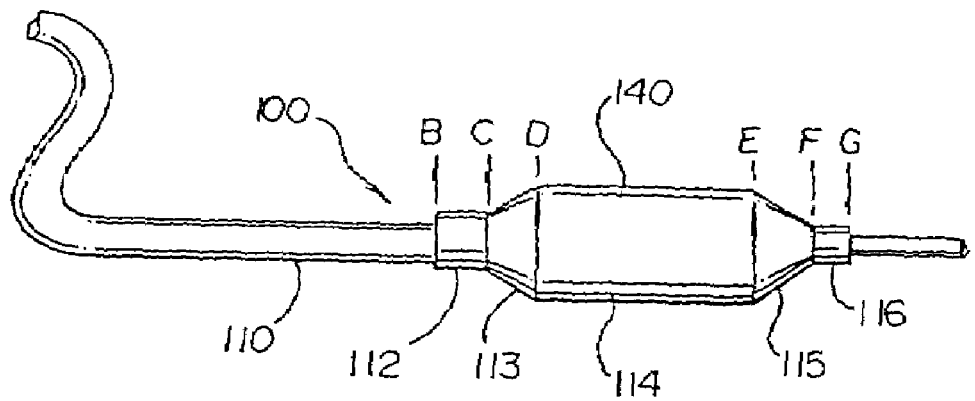
FIG. 1 is a perspective view of an angioplasty catheter having an example of a balloon fabricated from the inventive method mounted thereon.

The dilatation balloon fabricated by the present inventive method is illustrated generally at 100 in FIG. 1, mounted at the distal end of an elongated catheter 110. Catheter 110 is conventional in its construction, providing a lumen communicating with the interior of inflatable balloon, for inflation and deflation of the balloon, and other optional features conventional in the dilatation catheter art. The balloon 140 is in its inflated configuration. The balloon 140 is formed of a thermoplastic polymer material which provides the balloon with its essential compliance characteristics. It may be any thermoplastic polymer suitable for use as an angioplasty balloon material. Preferred materials include thermoplastic elastomers, suitably, polyamide elastomers, such as Pebax® 4033, 5533, 6333, 7033 or 7233 polyester/polyether elastomers such as Arnitel EM 740 (DSM Engineering), and polyurethane elastomers such as Pellethane 2102-80D. Other thermoplastic materials such as PET (polyethylene terephthalate), PBT (polybutylene terephthalate), Surlyn® (polyethylene ionomer), nylon, ethylene-vinyl acetate and others elsewhere described as useful for preparing balloons may be employed. Additional non-thermoplastic materials from which the balloon may be made include latex and PTFE.

As shown in FIG. 1, the balloon has several different regions including region B-C which comprises the proximal waist portion 112, region C-D which comprises the proximal cone portion 113, region D-E which comprises the body portion 114, region E-F which comprises the distal cone portion 115 and region F-G which comprises the distal waist portion 116.

Figure 2A:
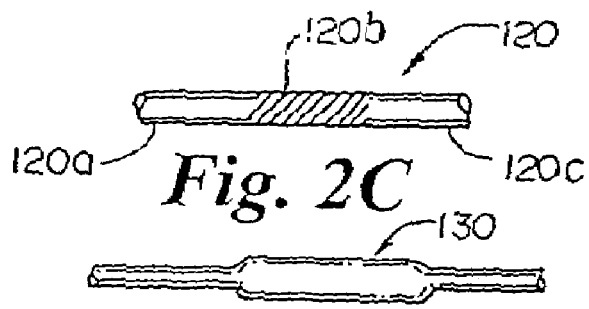
FIGS. 2a, 2b, 2c and 2d illustrate the results of various process steps in forming a catheter balloon, depicting respectively, side elevational views of a tube of polymer material used to form the balloon, the tube of FIG. 2a with material removed therefrom, a stretched polymer tubing preform prepared from the tube, and a formed balloon prepared from the stretched polymer tubing preform.
Figure 2C:
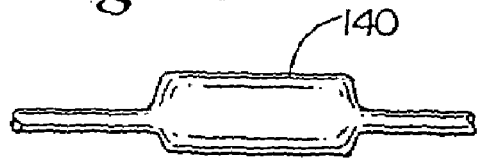
Figure 2D:
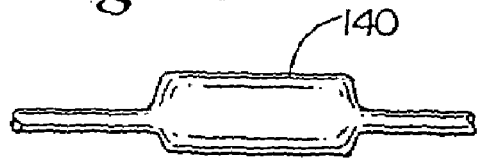

The method of the invention is performed by providing a segment of tubing 120, as shown in FIG. 2*a*, of a suitable balloon material. Desirably, the tubing is extruded. Any conventional extruder may be employed to extrude the tubing. While the tubing is desirably cylindrical, other shaped tubing may be used as well.

At least the center portion 120*b* of the polymer tubing 120, which eventually becomes the balloon, is maintained at a temperature below about the glass transition temperature of the tubing as described in more detail below. At this point the polymer tubing has three sections, a proximal end 120*a*, a distal end 120*c* and a center portion 120*b*.

Figure 2B:
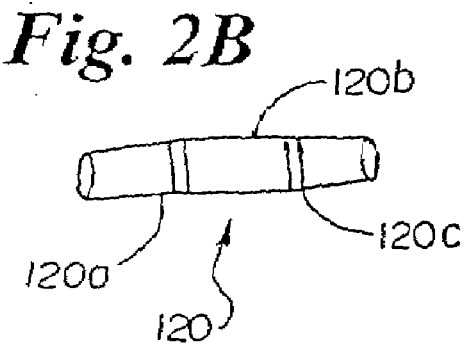

Polymer material from at least one of the proximal and distal end portions of the tubing 120 is removed to a desired thickness preferably while maintaining the temperature of at least a portion of the segment below about the glass transition temperature (Tg) of the thermoplastic material (or below about the highest glass transition temperature if the material is a block copolymer). Temperatures as high as 25° C. above Tg are contemplated. Desirably, the temperature will be maintained at Tg or below. As shown in FIG. 2*b*, material has been removed from both the proximal 120*a* and distal 120*c* end portions of the tubing 120. Desirably, the entire segment will be maintained below the glass transition temperature. Super-cooling the tube further below Tg, at the point where material is removed, may yield higher quality materials removal. Of course, where the glass transition temperature of the material is above room temperature, the material removal can be carried out at room temperature with no cooling or minimal cooling of the material.

The invention also contemplates removing material from the tubing at a temperature exceeding the glass transition temperature of the material. In the case of balloon materials which are not characterized by one or more glass transition temperatures, the invention in one aspect contemplates maintaining the material at a temperature below ambient and in another aspect contemplates materials removal at ambient temperature.

In one embodiment, material is removed from both the proximal and distal ends of the polymer tubing to a desired thickness. The amount of material removed from both ends may be the same or different.

Figure 3:
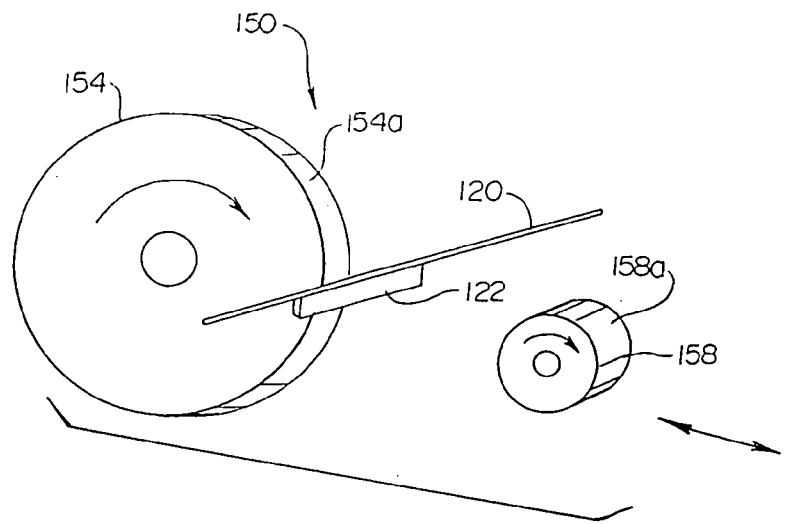
FIG. 3 is a schematic view of a centerless grinding device that may be useful in the practice of the method of the invention.

The material may be removed from the proximal and/or distal end portions of the segment by grinding. While any suitable grinding process may be employed, the segment desirably will be subject to a centerless grind. A schematic of a centerless grinder is shown in FIG. 3. Typically, a segment 120, supported on rest blade 122, is fed at one end into a centerless grinder, shown generally at 150, and guided between two grinding wheels (work wheel 154 and regulating wheel 158) that rotate in the same direction at different speeds. Segment 120 rotates as a result of its contact with regulating wheel 158 and is ground to a specified diameter or wall thickness dictated by the distance between the faces 154*a* and 158*a* of the two grinding wheels. One of the grinding wheels, typically the regulating wheel, may be moved so as to vary the distance between the faces of the grinding wheels during the grinding process. The segment advances through the grinding machine as a result of its contact with the grinding wheels. Specifically, one of the grinding wheels, typically the regulating wheel, rotates along an axis that is almost parallel to the axis of rotation of the segment being ground, but slightly skewed in a vertical plane, so that its contact with the segment causes the segment to move forward through the machine. A suitable centerless grinder which may be used is the Royal Master Grinder model number TG12X3.

As the segment moves forward through the grinder, the grinding action may be stopped and restarted at a later time thereby allowing for the proximal and distal ends to be ground without grinding the body portion of the segment.

Figure 4:
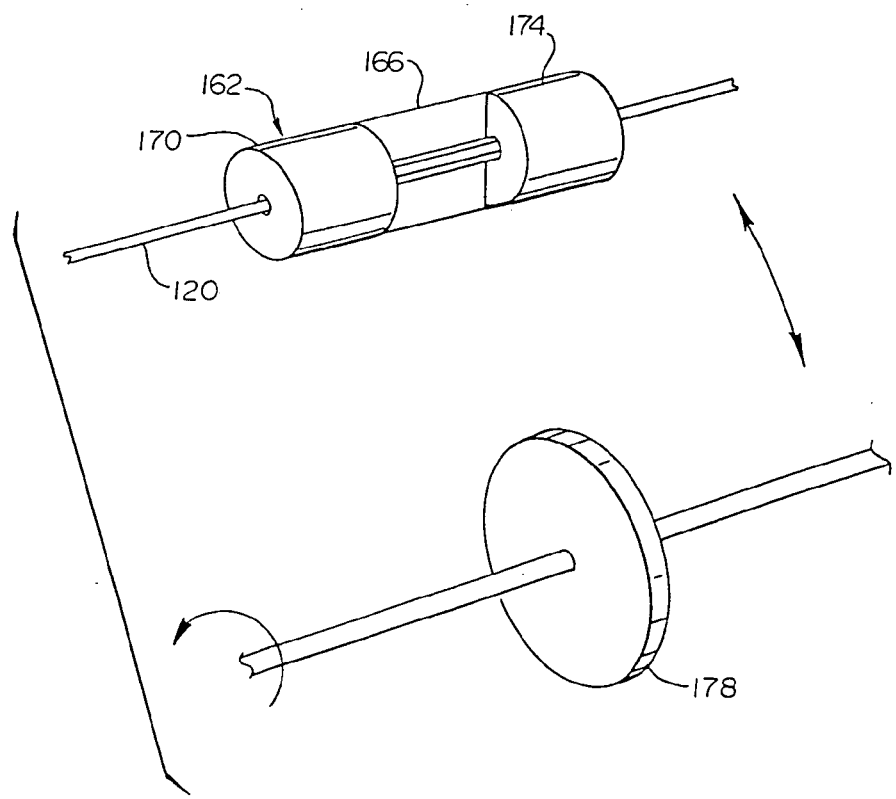
FIG. 4 is a schematic view of a benchtop grinder and die for use in grinding the balloon preform or balloon.

A number of factors affect the rate at which the segment moves through the grinding machine and the rate at which wheels must be changed. Temperature, regulating wheel rotation rate (in revolutions per minute—rpm), regulating wheel tilt angle, slippage, type of coolant used, grinding wheel material, segment diameter, segment material, and segment uniformity may affect the feed rate. As may be appreciated from the description of the centerless grinding process, having a straight and preferably uniform tubing segment is essential to effective centerless grinding.

Where the materials removal is accomplished by grinding with a benchtop grinder, the tubing segment 120 may be supported by a die of suitable length such as that shown in FIG. 4, that is fixed to the grinding machine. Desirably, the die, shown generally at 162, will be tubular with half of the die cut away in the middle third 166 of the die to provide access to the segment. The first 170 and second ends 174 of the die have a bore therethrough to allow the segment 120 to be held therein. Also desirably, there will be a minimal clearance between the outer diameter (OD) of the segment and the inner diameter (ID) of the die. A mandrel may also be used in place of or in addition to the die for support as needed.

Material is removed from segment 120 by applying rapidly rotating grinding wheel 178 to the segment. The grinding wheel is rotated at a suitable rate which will depend, inter alia, on the type of material, the amount of material to be removed, the type of grit on the grinding wheel and the availability of coolants. Rates of about 2000 revolutions per minute or higher have been found to be suitable. Tubing segment 120 is rotated within die 162 during the grinding process to ensure uniform material removal.

The segment may also be ground using other suitable devices such as a belt sander.

Desirably, as the segment is ground, a coolant is applied to the segment to prevent heating of the segment. A coolant such as water or saline may be misted onto the segment. Other suitable coolants including air and other gasses such as carbon dioxide, nitrogen, argon and chlorofluorocarbons may also be used. Additional, cryosprays as are known in the art may be used as well. Of course, if the glass transition temperature of the material is above room temperature, the grinding may be carried out at room temperature with no or minimal additional cooling of the segment.

Heating of the segment as a result of the material removal may also be controlled by altering the material removal rate. By slowing the rate of material removal such as by grinding, heat buildup in the segment may be reduced.

The grinding wheel used to grind the segment desirably employs a fine grit. A 120 mesh silicon carbide grit has proven suitable for use with Pebax®, PBT and PET balloons and balloon preforms although other size and type grits including diamond, silica and aluminum may also be suitable for PET and other balloon materials. With the use of such a grit, the resulting ground surface will be smooth thereby avoiding a cratered or otherwise irregular surface.

Other suitable techniques for removing material may also be employed such as chemical etching. In the case of chemical etching, a mask is applied to the segment except in the regions from which material is to be removed. Polymer etchant is then applied to the exposed portions of the segment so as to etch away a desired amount of tube material. The segment is then rinsed off and the mask removed.

The selective masking of the segment may be accomplished by a variety of suitable techniques as are known in the art.

Where material is removed from the waist portion, the desired thickness of the balloon waist portion will depend on how the balloon is affixed to the catheter. Where the balloon is adhesively bonded to the catheter, the thickness after the materials removal must be such that the waist section of the balloon will still have sufficient strength. Where the balloon is heat bonded to the catheter, the balloon may have a thinner waist without the strength limitations of adhesive bonds.

In either case, both distal and proximal ends will desirably be as thin as possible while still maintaining sufficient bond strength with the catheter shaft. A waist thickness of approximately 0.001" plus or minus 0.0004" is particularly desirable.

Because the distal waist portion of a balloon blow molds to a diameter less than the proximal waist portion, typically, in the absence of material removal the distal waist portion of the balloon will be thicker than the proximal waist portion. This difference in diameters should be taken into account in determining how much material should be removed from the various portions of the segment.

In a preferred embodiment, sufficient material is removed from the distal waist so that the distal waist is thinner than the proximal waist in order to achieve increased flexibility. Additionally, the proximal waist need not be as thin as the distal due to how the waist mates up with the rest of the catheter shaft.

The tube may then be formed into a balloon using known balloon forming techniques. One such suitable technique is disclosed in U.S. Pat. No. 5,807,520 to Wang et al.

Another suitable technique for forming the balloon involves prestretching the tube and expanding the tube into the form of a balloon by blow molding.

The segment of polymer tubing is optionally prestretched on either side of the center portion 120b by elongating proximal 120a and distal 120c ends axially. Referring to FIGS. 2a–d, the prestretching process comprises applying an axial stretching force to the polymer tubing 120, allowing the polymer tubing to stretch while maintaining the axial stretching force and finally allowing the stretched polymer tubing 70 to reach approximately room temperature. In so doing, the proximal and distal ends form a first and second waist, respectively.

Once the prestretch is complete, the stretched polymer tubing 70 is radially expanded into the form of a balloon 140 by using a molding process. The molding process comprises placing the stretched polymer tubing 70 in a mold, heating the mold and expanding the stretched polymer tubing radially by means of internal pressure. After sufficient time has passed for the balloon to form, the mold is cooled and the balloon 140 is removed.

The invention is also directed to the formation of a balloon by stretching a preform and subsequently removing material from the proximal and/or distal waist and/or cone portions of the balloon preform. The materials removal may also occur prior to or following blowing of the balloon and in one aspect of the invention, material is removed from a balloon that has already been formed.

Although any of the above materials removal techniques may be employed, it is desirable when grinding subsequent to stretching to hold the temperature of the preform below the glass transition temperature as described above. This technique may be particularly useful in the formation of Pebax®, PBT and PET balloons.

The invention is also directed to a medical balloon having a proximal waist portion, a proximal cone portion, a body portion, a distal cone portion and a distal waist portion wherein at least one of the proximal cone and waist wall thicknesses and distal cone and waist wall thicknesses is less than the body wall thickness, at least one of the proximal waist and cone portions and distal waist and cone portions having had material removed therefrom.

Where the wall thickness of the given portion is not constant, as with many balloons, desirably, the average wall thickness of at least one of the proximal cone and waist portions and distal cone and waist portions is less than the body wall thickness.

The invention is also directed to a medical balloon having a distal cone whose wall thickness is less than the wall thickness of the proximal cone. Where the wall thickness of the distal and proximal cones varies, desirably, the average wall thickness of the distal cone will be less than the average wall thickness of the proximal cone.

The invention is also directed to a medical balloon which when inflated to a desired pressure has a constant wall thickness over substantially the entire portion of the balloon including the cone and body portions. Such a balloon may be prepared by removing a sufficient amount of material from the proximal and/or distal waist and /or cone portions of the balloon.

The invention is illustrated by the following non-limiting examples. In each of the following examples, the distal and proximal ends of a tube were ground using a centerless grinder at room temperature. The tube was cooled using a water spray. Following grinding, the tube was stretched at room temperature until a visual change in the outer diameter of the tube was noticed. The tube was then oriented with the ground section in the cone region of a mold and lowered, ground portion first, into a 95° C. water bath. The tube was immersed to approximately the transition level between the ground and non-ground section. The first ground section was blown at a pressure of from about 350 to about 450 pounds per square inch (psi) to form the first cone and the mold was then immersed further into the water bath and the body section blown at a pressure of from about 300 to about 350 psi. Finally, the second ground portion was immersed in the bath and blown to form a second cone at a pressure of from about 350 to about 450 psi.

The following abbreviations and measurement units are used in the tables below:

ID—inner diameter (reported in inches)
OD—outer diameter (reported in inches)
1×Wall—total wall thickness (reported in inches) including inner wall and outer wall in the case of extruded tubing
Outer Wall—thickness of outer layer of extruded tubing (reported in inches)
Inner Wall—thickness of inner layer of extruded tubing (reported in inches)
Grind OD—Outer diameter of tube in ground region (reported in inches)
New Wall—Wall thickness in ground region as given by Grind (OD–ID)/2 (reported in inches)
% Grind—measure of percentage of material removed
Taper length—length of transition between ground and unground portions (reported in inches)

EXAMPLE 1

Figure 5A:
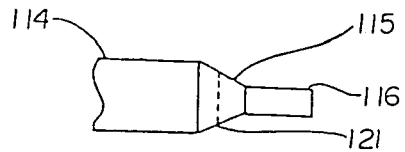
FIG. 5a is a schematic of a portion of a balloon with a grind transition half way along the cone.
Figure 5B:
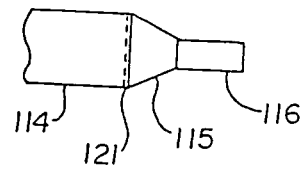
FIG. 5b is a schematic of a portion of a balloon with a grind transition at the body-cone interface.

Coextruded tubing (inner layer Pebax 7233, outer layer Pebax 4033) was ground in accordance with the present invention and formed into a balloon using the method described immediately above. Measurements were made for balloons formed from tubes with a grind transition 121 half way along the distal cone 115 (lower cone transition) shown schematically in FIG. 5a and tubes with a grind transition 121 at the distal cone 115 body 114 interface (upper cone transition) shown schematically in FIG. 5b. The wall thickness of the balloon was measured in the waist 116, half way along the cone and in the body portion 114 of the balloon. For the sake of comparison, measurements were made on a balloon formed from an unground tube as well (non-grind). The measurements were repeated on balloons formed from four separate tubes. Reported below in Table 1 are the measured single wall thicknesses in inches for samples 1–4. The properties of the initial tubes prior to blowing are reported in Table 2.

TABLE 1

| Sample | Distal | Coex Sample × $10^{-3}$ in | | | | ×$10^{-3}$ in |
|---|---|---|---|---|---|---|
| | | 1 | 2 | 3 | 4 | Avg. |
| Nongrind | Waist | 6.50 | 6.25 | 6.55 | 6.30 | 6.40 |
| | ½ cone | 1.95 | 2.00 | 2.10 | 2.40 | 2.11 |
| | body | 1.30 | 1.50 | 1.50 | 1.30 | 1.40 |
| Lower cone trans. | Waist | 3.35 | 3.10 | 3.30 | 3.10 | 3.21 |
| | ½ cone | 1.55 | 1.75 | 1.60 | 1.75 | 1.66 |
| | body | 1.40 | 1.55 | 1.40 | 1.50 | 1.46 |
| Upper cone trans. | Waist | 3.20 | 3.35 | 3.25 | 3.30 | 3.28 |
| | ½ cone | 1.50 | 1.35 | 1.50 | 1.50 | 1.46 |
| | body | 1.40 | 1.50 | 1.55 | 1.55 | 1.50 |

TABLE 2

| ID | OD | 1 × Wall | Outer Wall | Inner Wall | Grind OD | New wall | % Grind | Taper Length |
|---|---|---|---|---|---|---|---|---|
| 0.0185 | 0.0453 | 0.0134 | 0.0054 | 0.0080 | 0.0383 | 0.0099 | 26% | .0136 |

The balloons of example 1 had a cone length of 2.5 mm and a cone angle of 45°.

EXAMPLE 2

Figure 6A:
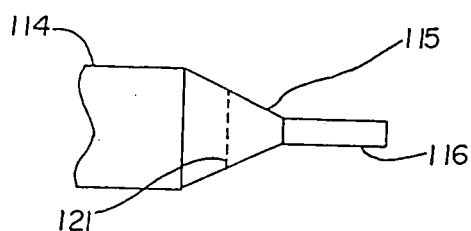
FIG. 6a is a schematic of a portion of a balloon with a grind transition two thirds of the way along the cone.
Figure 6B:
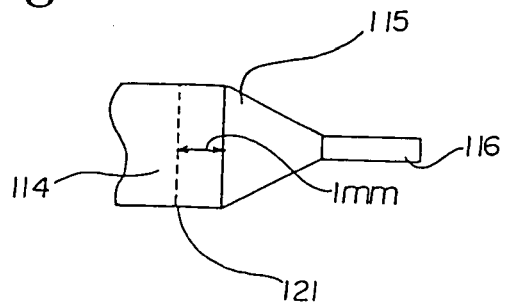
FIG. 6b is a schematic of a portion of a balloon with a grind transition at the body-cone interface.

Polybutyleneteraphthalate (PBT) tubing was ground in accordance with the present invention and formed into a balloon using the method described above. The wall thickness of the balloon was measured in the waist, one third of the way along the cone, two thirds of the way along the cone and in the body portion of the balloon. As shown schematically in FIGS. 6a and 6b, measurements were made for balloons formed from tubes with a grind transition 121 two thirds of the way along the distal cone 115 and tubes with a grind transition 121 at the distal cone 115—body 114 interface (upper cone transition). For the sake of comparison, measurements were made on a balloon formed from an unground tube as well (non-grind). The measurements were repeated on four separate tubes. Reported below in Table 3a are the measured single wall thicknesses in inches.

Measurements were also made on PBT balloons with proximal cones ground as described above and reported below in Table 3b.

The properties of the initial tubes are reported in Table 4.

TABLE 3a

| | Distal | PBT Sample × $10^{-3}$ in | | | | ×$10^{-3}$ in |
|---|---|---|---|---|---|---|
| | | 1 | 2 | 3 | 4 | Avg |
| Control | Waist | 2.80 | 2.90 | 2.90 | 2.85 | 2.86 |
| | ⅓ cone | 1.55 | 1.30 | 1.50 | 1.50 | 1.46 |
| | ⅔ cone | 1.05 | 0.95 | 0.95 | 0.95 | 0.98 |
| | body | 0.75 | 0.65 | 0.75 | 0.70 | 0.71 |
| Cone Trans. | Waist | 1.70 | 1.75 | 1.85 | 1.85 | 1.79 |
| | ⅓ cone | 0.90 | 0.95 | 1.00 | 1.00 | 0.96 |
| | ⅔ cone | 0.70 | 0.65 | 1.00 | 0.95 | 0.83 |
| | body | 0.75 | 0.65 | 0.70 | 0.75 | 0.71 |
| Body Trans. | Waist | 1.95 | 1.80 | 1.95 | 1.85 | 1.89 |
| | ⅓ cone | 0.95 | 0.95 | 1.00 | 0.80 | 0.93 |
| | ⅔ cone | 0.65 | 0.50 | 0.50 | 0.40 | 0.51 |
| | body unground | 0.75 | 0.65 | 0.70 | 0.75 | 0.71 |
| | body ground | 0.35 | 0.40 | 0.40 | 0.30 | 0.36 |

TABLE 3b

| | Proximal | PBT Sample × $10^{-3}$ in | | | | ×$10^{-3}$ in |
|---|---|---|---|---|---|---|
| | | 1 | 2 | 3 | 4 | Avg. |
| Nongrind | Waist | 2.25 | 2.25 | 2.0 | 2.40 | 2.30 |
| | ⅓ cone | 1.50 | 1.65 | 1.5 | 1.60 | 1.58 |
| | ⅔ cone | 1.00 | 1.15 | 0.5 | 0.85 | 0.99 |
| | body | 0.70 | 0.75 | 0.70 | 0.70 | 0.71 |
| Cone Trans. | Waist | 1.40 | 1.65 | 1.25 | 1.45 | 1.44 |
| | ⅓ cone | 1.50 | 1.70 | 1.50 | 1.30 | 1.50 |
| | ⅔ cone | 0.90 | 1.10 | 1.00 | 1.00 | 1.00 |
| | body | 0.70 | 0.75 | 0.70 | 0.65 | 0.70 |

TABLE 4

| ID | OD | 1 × Wall | Grind OD | New Wall | % Grind | Taper Length |
|---|---|---|---|---|---|---|
| 0.0150 | 0.0380 | 0.0115 | 0.032 | 0.0085 | 26% | 0.03 |

The balloons of example 2 had a cone length of 4.0 mm and a cone angle of 15°.

EXAMPLE 3

Figure 7:
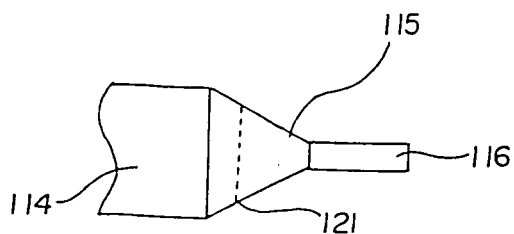
FIG. 7 is a schematic of a portion of a balloon with a grind transition two thirds of the way along the cone.

Pebax 7233 tubing was ground in accordance with the present invention and formed into a balloon using the method described above. The wall thickness of the balloon was measured in the waist, one third of the way along the cone, two thirds of the way along the cone and in the body portion of the balloon. Measurement were made for balloons formed from tubes with a 30% wall grind and a 40% wall grind. As shown schematically in FIG. 7, the grind transition 121 was ⅔ of the way along the distal cone 115. For the sake of comparison, measurements were made on a balloon formed from an unground tube as well (non-grind). The measurements were repeated on four separate tubes. Reported below in Table 5 are the measured single wall thicknesses in inches.

The properties of the initial tubes are reported in Table 6.

TABLE 5

| | Distal | Quantum Sample × $10^{-3}$ in | | | | ×$10^{-3}$ in |
|---|---|---|---|---|---|---|
| | Nongrind | 1 | 2 | 3 | 4 | Avg. |
| | Waist | 3.70 | 3.85 | 3.70 | 3.45 | 3.68 |
| | ⅓ cone | 2.10 | 2.40 | 2.50 | 2.45 | 2.36 |
| | ⅔ cone | 1.00 | 1.35 | 1.25 | 1.30 | 1.23 |
| | body | 0.75 | 0.85 | 0.85 | 0.75 | 0.80 |
| 24% wall | Waist | 3.10 | 3.15 | 2.80 | 3.05 | 3.03 |
| | ⅓ cone | 1.25 | 1.60 | 1.20 | 1.20 | 1.31 |
| | ⅔ cone | 1.00 | 1.10 | 1.05 | 1.00 | 1.04 |
| | body | 0.85 | 0.85 | 0.85 | 0.90 | 0.86 |
| 34% wall ground | Waist | 2.10 | 2.10 | 1.80 | 2.20 | 2.05 |
| | ⅓ cone | 0.55 | 0.60 | 0.55 | 0.65 | 0.59 |
| | ⅔ cone | 0.90 | 0.95 | 0.11 | 0.90 | 0.96 |
| | body | 0.85 | 0.85 | 0.85 | 0.90 | 0.86 |

TABLE 6

| ID | OD | 1 × Wall | Grind OD | New Wall | % Grind | Taper Length |
|---|---|---|---|---|---|---|
| 0.019 | 0.036 | 0.0085 | 0.0309 | 0.0060 | 30% | 0.03 |
| 0.019 | 0.036 | 0.0085 | 0.0292 | 0.0051 | 40% | 0.03 |

The balloons of example 1 had a cone length of 4.0 mm and a cone angle of 15°.

EXAMPLE 4

Figure 8:
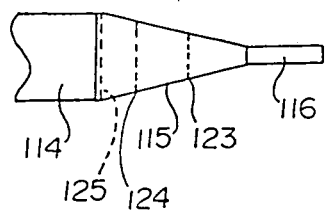
FIG. 8 is a schematic of a portion of an inventive balloon.

Pebax 7233 tubing was ground in accordance with the present invention and formed into a balloon using the method described above. The wall thickness of the balloon was measured in the waist, one third of the way along the cone, two thirds of the way along the cone and in the body portion of the balloon. Measurements were made for balloons formed from tubes with a 24% wall grind and a 35% wall grind. Tubes were ground with a 32 mm backoff and a 33 mm backoff. As shown in FIG. 8, the 31 mm backoff line is indicated by reference numeral 123, the 32 mm backoff line is indicated by reference numeral 124 and 33 mm backoff line is indicated by reference numeral 125. For the sake of comparison, measurements were made on a balloon formed from an unground tube as well (non-grind). The measurements were repeated on four separate tubes. Reported below in Tables 7a–d are the measured single wall thicknesses in inches for balloons formed from tubes with a 30% distal grind and 30% proximal grind and for balloons formed from tubes with a 40% distal grind and 20% proximal grind.

The properties of the initial tubes are reported in Table 8.

TABLE 7a

| | | Grind Distal 30% Proximal 30% | | | | |
|---|---|---|---|---|---|---|
| | Distal | 5.0 Leap II Sample × $10^{-3}$ in | | | | ×$10^{-3}$ in |
| | Portion | 1 | 2 | 3 | 4 | Avg |
| Nongrind | 0 | 5.25 | 5.85 | 5.35 | 5.35 | 5.45 |
| | 1 | 2.90 | 1.80 | 2.80 | 1.90 | 2.35 |
| | 2 | 1.95 | 1.30 | 1.85 | 1.55 | 1.66 |
| | 3 | 1.40 | 1.10 | 1.35 | 1.20 | 1.26 |
| | 4 | 1.10 | 1.00 | 1.10 | 1.10 | 1.08 |
| | 5 | 0.85 | 0.80 | 0.95 | 1.00 | 0.90 |
| 32 mm backoff | 0 | 3.80 | 3.75 | 3.50 | 3.55 | 3.65 |
| | 1 | 1.80 | 1.90 | 1.75 | 1.85 | 1.83 |
| | 2 | 1.20 | 1.40 | 1.05 | 1.60 | 1.31 |
| | 3 | 0.90 | 1.00 | 0.90 | 0.85 | 0.91 |
| | 4 | 1.05 | 1.05 | 1.10 | 1.00 | 1.05 |
| | 5 | 0.95 | 1.05 | 0.95 | 0.95 | 0.98 |
| 33 mm backoff | 0 | 3.60 | 3.60 | 3.75 | 3.70 | 3.65 |
| | 1 | 2.10 | 1.95 | 1.90 | 1.85 | 1.95 |
| | 2 | 0.75 | 1.00 | 1.00 | 0.95 | 0.90 |
| | 3 | 0.95 | 0.75 | 0.80 | 0.85 | 0.84 |
| | 4 | 0.90 | 0.90 | 0.85 | 0.90 | 0.89 |
| | 5 | 1.00 | 1.00 | 1.00 | 1.05 | 1.01 |

TABLE 7b

| | | Grind Distal 30% Proximal 30% | | | | |
|---|---|---|---|---|---|---|
| | Proximal | 5.0 Leap II Sample × $10^{-3}$ in | | | | ×$10^{-3}$ in |
| | Portion | 1 | 2 | 3 | 4 | Avg |
| Nongrind | 0 | 5.35 | 5.00 | 4.75 | 4.75 | 4.96 |
| | 1 | 2.95 | 3.25 | 2.70 | 3.00 | 2.98 |
| | 2 | 2.05 | 1.80 | 1.75 | 1.95 | 1.89 |
| | 3 | 1.30 | 1.30 | 1.25 | 1.25 | 1.28 |
| | 4 | 1.10 | 1.15 | 1.00 | 1.10 | 1.09 |
| | 5 | 1.05 | 1.00 | 1.00 | 1.00 | 1.01 |
| 32 mm backoff | 0 | 2.30 | 2.75 | 2.75 | 2.70 | 2.63 |
| | 1 | 1.45 | 1.95 | 1.65 | 1.80 | 1.71 |
| | 2 | 1.05 | 1.30 | 1.05 | 1.20 | 1.15 |
| | 3 | 0.80 | 0.95 | 0.85 | 0.85 | 0.86 |
| | 4 | 0.70 | 0.75 | 0.70 | 0.60 | 0.69 |
| | 5 | 1.00 | 1.05 | 1.00 | 1.00 | 1.01 |
| 33 mm backoff | 0 | 2.90 | 2.45 | 2.60 | 2.70 | 2.66 |
| | 1 | 2.05 | 1.45 | 1.65 | 2.00 | 1.79 |
| | 2 | 1.50 | 1.05 | 1.15 | 1.25 | 1.24 |
| | 3 | 1.00 | 0.75 | 0.90 | 0.85 | 0.88 |
| | 4 | 0.75 | 0.65 | 0.65 | 0.70 | 0.69 |
| | 5 | 1.10 | 1.00 | 1.05 | 0.75 | 0.98 |

TABLE 7c

Grind Distal 40% Proximal 20%

| | Distal | 5.0 Leap II Sample × $10^{-3}$ in | | | | ×$10^{-3}$ in |
|---|---|---|---|---|---|---|
| | | 1 | 2 | 3 | 4 | Avg |
| Nongrind | 0 | 5.25 | 5.85 | 5.35 | 5.35 | 5.45 |
| | 1 | 2.90 | 1.80 | 2.80 | 1.90 | 2.35 |
| | 2 | 1.95 | 1.30 | 1.85 | 1.55 | 1.66 |
| | 3 | 1.40 | 1.10 | 1.35 | 1.20 | 1.26 |
| | 4 | 1.10 | 1.00 | 1.10 | 1.10 | 1.08 |
| | 5 | 0.85 | 0.80 | 0.95 | 1.00 | 0.90 |
| 31 mm backoff | 0 | 2.30 | 2.40 | 2.30 | 2.40 | 2.35 |
| | 1 | 1.05 | 1.45 | 1.00 | 1.25 | 1.19 |
| | 2 | 1.15 | 1.35 | 1.20 | 1.20 | 1.23 |
| | 3 | 1.15 | 1.20 | 1.10 | 1.20 | 1.16 |
| | 4 | 1.05 | 1.10 | 1.05 | 1.05 | 1.06 |
| | 5 | 0.95 | 1.00 | 0.95 | 1.00 | 0.98 |
| 32 mm backoff | 0 | 2.40 | 2.45 | 2.50 | 2.40 | 2.44 |
| | 1 | 1.30 | 1.30 | 1.30 | 1.00 | 1.23 |
| | 2 | 0.85 | 0.80 | 1.00 | 0.85 | 0.88 |
| | 3 | 0.95 | 0.95 | 1.10 | 1.00 | 1.00 |
| | 4 | 1.00 | 1.00 | 1.05 | 0.95 | 1.00 |
| | 5 | 1.00 | 1.00 | 0.95 | 0.95 | 0.98 |

TABLE 7d

Grind Distal 40% Proximal 20%

| | Proximal Portion | 5.0 Leap II Sample × $10^{-3}$ in | | | | ×$10^{-3}$ in |
|---|---|---|---|---|---|---|
| | | 1 | 2 | 3 | 4 | Avg |
| Nongrind | 0 | 5.35 | 5.00 | 4.75 | 4.75 | 4.96 |
| | 1 | 2.95 | 3.25 | 2.70 | 3.00 | 2.98 |
| | 2 | 2.05 | 1.80 | 1.75 | 1.95 | 1.89 |
| | 3 | 1.30 | 1.30 | 1.25 | 1.25 | 1.28 |
| | 4 | 1.10 | 1.15 | 1.00 | 1.10 | 1.09 |
| | 5 | 1.05 | 1.00 | 1.00 | 1.00 | 1.01 |
| 31 mm backoff | 0 | 3.60 | 3.70 | 3.70 | 3.70 | 3.68 |
| | 1 | 2.10 | 2.40 | 2.20 | 2.25 | 2.24 |
| | 2 | 1.40 | 1.45 | 1.30 | 1.40 | 1.39 |
| | 3 | 1.00 | 1.00 | 1.05 | 1.00 | 1.01 |
| | 4 | 0.95 | 0.90 | 1.00 | 1.00 | 0.96 |
| | 5 | 1.05 | 1.00 | 1.05 | 1.05 | 1.04 |
| 32 mm backoff | 0 | 3.40 | 3.65 | 3.70 | 3.60 | 3.59 |
| | 1 | 2.05 | 2.40 | 2.45 | 1.90 | 2.20 |
| | 2 | 1.40 | 1.50 | 1.45 | 1.20 | 1.39 |
| | 3 | 1.05 | 1.15 | 1.10 | 1.00 | 1.08 |
| | 4 | 1.05 | 1.10 | 1.05 | 1.10 | 1.08 |
| | 5 | 1.10 | 1.05 | 1.05 | 1.00 | 1.05 |

TABLE 8

| ID | OD | 1 × Wall | Grind OD | New Wall | % Grind | Taper Length |
|---|---|---|---|---|---|---|
| | | | Distal | | | |
| 0.0334 | 0.055 | 0.0108 | 0.0499 | 0.0083 | 24% | 0.04 |
| 0.0334 | 0.055 | 0.0108 | 0.0474 | 0.0070 | 35% | 0.04 |
| | | | Proximal | | | |
| 0.0334 | 0.055 | 0.0108 | 0.0518 | 0.0092 | 15% | 0.03 |

The balloons of example 1 had a cone length of 7.5 mm and a cone angle of 15°.

EXAMPLE 5

A balloon made of tubing subject to a 30% grind at the distal end, a balloon made of tubing subject to a 30% grind at both the distal and proximal ends, a balloon made of tubing subject to a 40% grind at the distal end and a control balloon made of non-ground tubing were subjected to a tensile test. The force required to pull a balloon cone through a predetermined orifice size at a constant rate of travel was measured for each of the balloons. The balloons were pulled at a rate of 5 inches per second with a one hundred pound load cell. The orifice diameter was 0.042 inches and the ratio of the distal outer diameter to the orifice diameter was 0.70. The gauge length was 10 mm.

Figure 9:
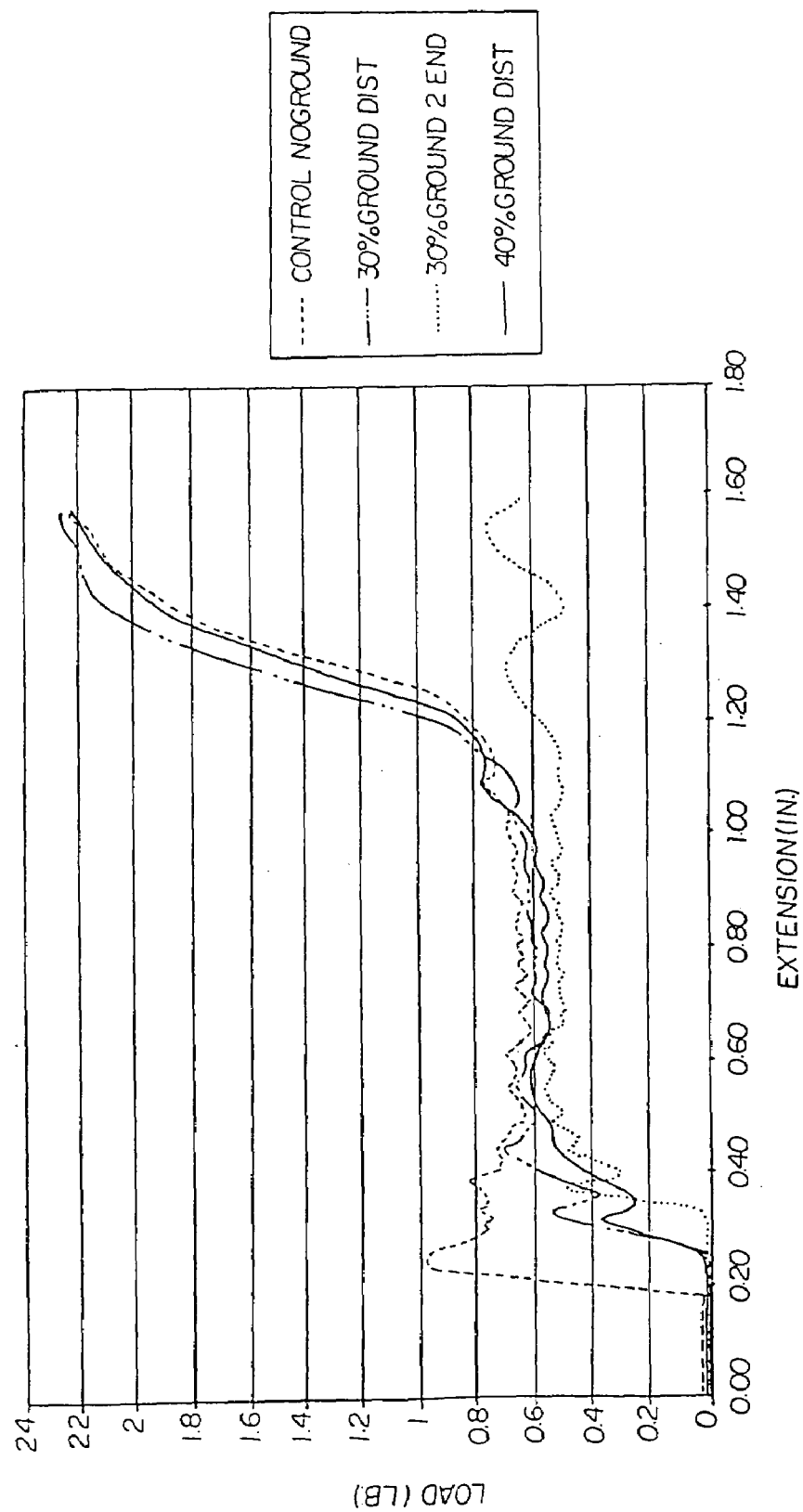
FIG. 9 shows the relationship between load and extension for a control balloon and several inventive balloons.

As shown in FIG. 9, the peak force required to pull the control balloon through the orifice as its distal cone enters the orifice is far in excess of the peak force required for the inventive balloons. Reductions in force can exceed 50%. Similarly, as the proximal cones pass through the orifice, the balloon which has been ground in the proximal cone region requires a significantly lower load (in excess of 50%) to pass through the orifice.

The instant example demonstrates that balloons formed in accordance with the instant invention may exhibit reduced cone and waist stiffness. Other benefits that may result from the inventive balloons include better balloon folding capability, lower balloon profile, greater tip flexibility and improved retraction performance of retaining sleeves which are often placed about the cones of a balloon.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A method comprising the steps of:
providing a medical balloon at least partially constructed of a thermoplastic material, the medical balloon having a predetermined wall thickness and length, the balloon having a proximal end portion, a distal end portion and a center portion;
removing material from a portion of at least one of the distal and proximal end portions of the balloon to a desired reduced thickness while maintaining the temperature of the entire balloon below about the glass transition temperature of the thermoplastic material or below the highest glass transition temperature of the thermoplastic material if the material is a block copolymer.

2. The method of claim 1 wherein material is removed from a portion of the proximal end of the balloon to a desired thickness, wherein the portion of the proximal end consists of a proximal balloon waist, a proximal balloon cone, and any combination thereof.

3. The method of claim 1 wherein material is removed from a portion of the distal end of the balloon to a desired thickness, wherein the portion of the distal end consists of a distal balloon waist, a distal balloon cone, and any combination thereof.

4. The method of claim 1 wherein the at least one of the distal and proximal end portions of the balloon consist of at least one member of the group consisting of a proximal balloon waist, a distal balloon waist, a proximal balloon cone, a distal balloon cone and any combination thereof.

5. The method of claim 1 wherein the material is removed by a process selected from the group consisting of grinding, chemical etching and any combination thereof.

6. The method of claim 1 wherein after the removing step the wall thickness of the center portion is greater than the wall thickness of the at least one end portion from which material is removed.

7. The method of claim 1 wherein after the removing step the wall thickness of the center portion is greater than the wall thickness of the at least one of the distal and proximal end portions of the balloon.

8. The method of claim 1 wherein after the removing step, the thickness of the proximal end portion and the thickness of the distal end portion differ.

9. The method of claim 1 wherein material is removed from both the proximal end portion and distal end portion to desired thicknesses during the removing step.

10. The method of claim 9 wherein the coolant is selected from the group consisting of water, air, compressed gasses and any combinations thereof.

11. The method of claim 1 wherein a coolant is directed at the balloon during the removing step.

12. The method of claim 1 wherein the portion from which material is removed is maintained at a temperature cooler than the remainder of the balloon.

13. The method of claim 1, wherein the thermoplastic material is chosen from the group consisting of polyamide elastomers, polyester elastomers, polyamides, polyesters, polyethylenes, polyurethanes, polyethylene ionomers, and ethylene vinyl acetates.

14. The method of claim 1, wherein the thermoplastic material comprises a block copolymer.

15. The method of claim 1, wherein the step of providing a medical balloon further comprises providing a parison and stretching the parison to form the balloon.

16. The method of claim 1, wherein the step of removing material comprises removing material from an outer surface of the balloon.

17. A method comprising the steps of:
providing a medical balloon of thermoplastic material having a predetermined wall thickness and length, the balloon having a proximal end portion, a distal end portion and a center portion;
removing material from at least one portion of the proximal end and distal end portions of the balloon to a desired reduced thickness, while maintaining the temperature of substantially all of the balloon below a glass transition temperature of the thermoplastic material, wherein the material is removed by a process selected from the group consisting of grinding chemical etching and any combination thereof.

18. The method of claim 17 wherein the thermoplastic material comprises a block copolymer and the temperature of substantially all of the balloon is maintained below the highest glass transition temperature of the thermoplastic material during the removing step.

19. The method of claim 17 wherein the step of removing material comprises removing material from an outer surface of the balloon.

20. The method of claim 17 wherein the balloon has a substantially constant wall thickness over substantially its entire length after said material removal step.

21. The method of claim 14, wherein the step of providing a medical balloon further comprises providing a parison and stretching the parison to form the balloon.

* * * * *